United States Patent
Craig (10) Patent No.: US 11,135,330 B1
(45) Date of Patent: Oct. 5, 2021

(54) SYSTEM AND METHOD FOR DISINFECTING A STRUCTURE

(71) Applicant: Keith A. Craig, Silver Springs, FL (US)

(72) Inventor: Keith A. Craig, Silver Springs, FL (US)

( * ) Notice: Subject to any disclaimer, the term of this patent is extended or adjusted under 35 U.S.C. 154(b) by 0 days.

(21) Appl. No.: 17/108,723

(22) Filed: Dec. 1, 2020

Related U.S. Application Data (60) Provisional application No. 63/108,933, filed on Nov. 3, 2020.

(51) Int. Cl.
| | | |
|---|---|---|
| *A61L 2/22* | (2006.01) | |
| *A62C 35/68* | (2006.01) | |
| *A62C 35/58* | (2006.01) | |
| *A61L 2/24* | (2006.01) | |

(52) U.S. Cl.
CPC ........ *A61L 2/22* (2013.01); *A61L 2/24* (2013.01); *A62C 35/68* (2013.01); *A61L 2202/14* (2013.01); *A61L 2202/15* (2013.01)

(58) Field of Classification Search
CPC ............ A61L 2/22; A62C 35/68; A62C 35/58
See application file for complete search history.

(56) References Cited

U.S. PATENT DOCUMENTS

| | | | | |
|---|---|---|---|---|
| 6,296,808 B1 * | 10/2001 | Pearman | ............... | A62C 15/00 134/105 |
| 8,303,905 B2 | 11/2012 | Brents et al. | | |

FOREIGN PATENT DOCUMENTS

JP      2012000178 A  *  1/2012

OTHER PUBLICATIONS

English Translation of Japanese Document No. JP 2012000178A provided by the European Patent Office espacenet.com: Takeshi; Sprinkler Equipment; Jan. 5, 2012 (Year: 2012).*

* cited by examiner

*Primary Examiner* — Kevin Joyner
(74) *Attorney, Agent, or Firm* — Dale J. Ream (57) ABSTRACT

A disinfecting system for sanitizing a structure having a fire suppression sprinkler system includes a main conduit positioned in the structure and that is in fluid communication with a water source and operable to carry a water stream downstream from the water source. The disinfecting system includes a disinfectant conduit having in fluid communication with a disinfectant reservoir and operable to carry a disinfectant stream downstream from the disinfectant reservoir, the disinfectant conduit being in fluid communication with the main conduit. A control valve is in fluid communication with the disinfectant main conduits, the control valve allowing one of the disinfectant or water streams to flow downstream in the main conduit. A master nozzle defining outlet holes is in fluid communication with the main conduit, is positioned downstream of the control valve, and is operably configured to spray a liquid into an interior area of the structure.

9 Claims, 7 Drawing Sheets

SYSTEM AND METHOD FOR DISINFECTING A STRUCTURE

REFERENCE TO RELATED APPLICATIONS

This application claims the priority of provisional patent application U.S. Ser. No. 63/108,933 filed Nov. 3, 2020, titled System and Method for Disinfecting a Structure and which is incorporated in its entirety herein by reference.

BACKGROUND OF THE INVENTION

This invention relates generally to disinfectant systems and, more particularly, to a system in which fluid streams of water and disinfectant are transported individually to respective nozzles through a unitary pipe. More particularly, a fire-avoidance sprinkler system may be retrofit to selectively deliver water to a plurality of water sprinkler nozzles or a disinfectant solution to a plurality of disinfectant nozzles.

In times of the "pandemic of 2020" and for the foreseeable future, it will be important to keep school classrooms clean and sanitized in an effort to protect children and teachers from contracting a virus, especially a viral disease as contagious and deadly as the COVID-19 strain of a Corona virus. The CDC and politicians publicly recommend frequent hand washing, wearing masks, social distancing, and possible lockdowns and testing. In addition, it is generally seen as advantageous to keep public facilities disinfected and surfaces sanitized. For example, restaurants are sanitizing tables and chairs after every guest. Likewise, it would advantageous to routinely disinfect the desks and chairs of students and teachers in a school classroom and, frankly, in every room of a school.

In another aspect, public facilities often have ceiling-mounted sprinkler systems designed to spray large volumes of water on all surfaces of a room if heat, fire, or smoke indicative of a fire is detected in the proximity of the nozzle. Specifically, each nozzle includes its own heat sensitive valve and is designed to activate dispersion of water upon experiencing a predetermined temperature or a predetermined rate of rise in temperature.

Various proposals have been made for selectively disinfecting an enclosed area, such as a school classroom using piping and disinfectant liquid misting nozzles. Although presumably effective for their intended purposes, the existing proposals are complicated and expensive in that the sprinkler and disinfectant systems are largely separate and unconnected or unassociated with one another. Separate piping systems and systems unassociated with a unitary controller may be twice the cost and introduces the potential of a fire being made more intense if a disinfecting procedure is underway when a fire is detected.

Therefore, it would be desirable to have a system and method for disinfecting a structure that delivers a non-flammable disinfectant to a plurality of nozzles for dispersion on the structure. Further, it would be desirable to have a system and method for disinfecting a structure that carries a water stream and a disinfectant stream through a unitary piping assembly. In addition, it would be desirable to have a system and method for disinfecting a structure that immediately stops a disinfecting modality in favor of a fire suppression modality if a fire event is indicated.

SUMMARY OF THE INVENTION

A disinfecting system for sanitizing a structure of a type having a fire suppression sprinkler system according to the present invention includes a main conduit positioned in the structure and that has a first water segment in fluid communication with a water source and operable to carry a water stream downstream from the water source, the main conduit having a second segment downstream from the first segment. The disinfecting system includes a disinfectant assembly that includes a disinfectant conduit having a first end in fluid communication with a disinfectant reservoir and operable to carry a disinfectant stream downstream from the disinfectant reservoir, the disinfectant conduit having a second end downstream from the first end in fluid communication with the main conduit.

A control valve is positioned inline in the main conduit and in fluid communication with the second end the disinfectant conduit and in fluid communication with the second segment of the main conduit, the control valve being configured to allow one of the disinfectant stream or the water stream to flow downstream in the main conduit. A controller is in data communication with the control valve that is configured to determine whether to actuate the control valve to selectively allow the disinfectant stream or the water stream to flow downstream in the main conduit. A master nozzle having a plurality of outlet holes is situated along and in fluid communication with the main conduit, the master nozzle being positioned downstream of the control valve and operably configured to spray a liquid into an interior area of the structure.

Therefore, a general object of this invention is to provide a disinfecting system installed in cooperation with a fire suppression system and configured to mist a disinfectant solution into the structure, such as into a school classroom.

Another object of this invention is to provide a disinfecting system, as aforesaid, that carries a water stream and a disinfectant stream to a master nozzle via a unitary main conduit.

Still another object of this invention is to provide a disinfecting system, as aforesaid, in which fire suppression is a default mode and will always take priority over periodic disinfecting.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1b is an isolated view on an enlarged scale taken from FIG. 1a;

FIG. 1c is an isolated view on an enlarged scale taken from FIG. 1a;

FIG. 2a is a bottom perspective view of a master nozzle removed from the system of FIG. 1a;

DESCRIPTION OF THE PREFERRED EMBODIMENT

Figure 4:
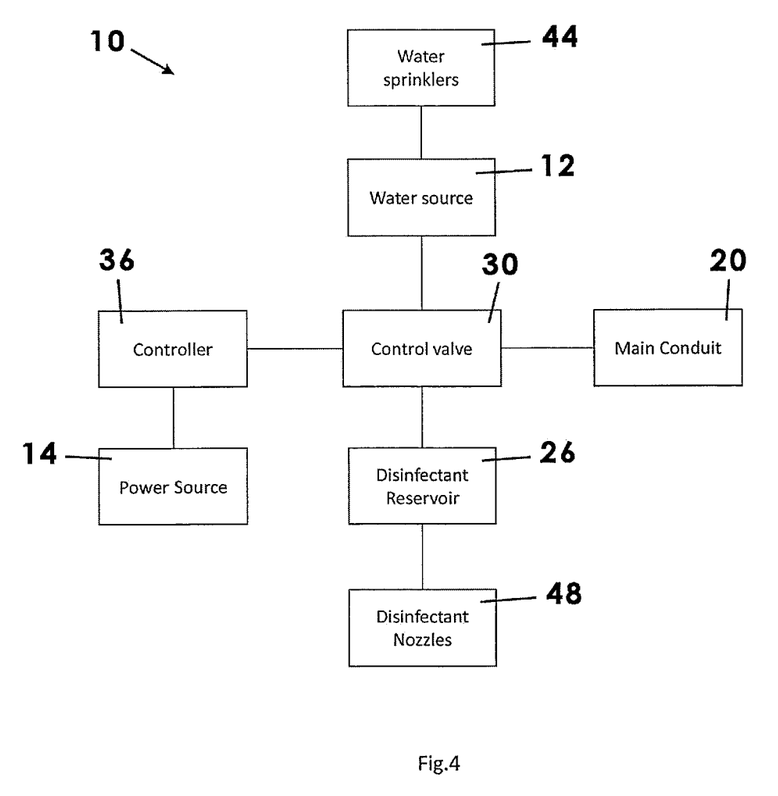
FIG. 4 is a block diagram illustrating conduit and electrical components of the present invention.

A system and method for disinfecting a structure 8 of a type having a fire suppression system (i.e. a sprinkler system) according to a preferred embodiment of the present invention will now be described with reference to FIG. 1a to 5 of the accompanying drawings. The major components, electrical, and electronic components of the disinfectant system 10 according to present invention are illustrated in FIG. 4.

The disinfecting system 10 includes a main conduit 20 operable to carry a water stream between a water source 12 and a sprinkler system. More particularly, the main conduit 20 is mounted in the structure and is the primary means for carrying a water stream. More particularly, the disinfecting system 10 includes a water assembly 21 having a first segment 22 in fluid communication with a water source 12 (such as a municipal water line) and operable to carry a water stream downstream from said water source 12. The water conduit 21 includes a second segment 24 downstream of the first segment 22 that is in fluid communication with the main conduit 20. As will be described in more detail later, the disinfecting system 10 includes one or more control valves for regulating flow directions of the water and disinfectant streams. It will be understood that there are other control valves for directing fluids as well and which may be in communication with the controller 36.

Similarly, the disinfecting system 10 includes a disinfectant assembly that includes a disinfectant conduit 25 having a first end 26 in fluid communication with a disinfectant reservoir 26 and is operable to carry a disinfectant stream downstream from said disinfectant reservoir 26. Further, the disinfectant conduit 25 includes a second end 28 downstream from the first end 26 so that the disinfectant stream flowing from the disinfectant reservoir 26 is in fluid communication with said main conduit 20 pursuant to operation of the control valve 31. More particularly, the second end 28 of the disinfectant conduit 25 may be connected to the control valve 31 where it, along with the water source 12, is in fluid communication with the first segment 22 of the main conduit 20.

Stated in more detail, the control valves 30 and 31 are positioned inline with the water source 12 and the disinfectant reservoir 26, respectively, so that respective conduits from both may be accessed thereby, according to instructions programmed into or accessed by a controller 36. More particularly, the control valve 31 is in fluid communication with the second end 28 of the disinfectant conduit 25 so as to receive a disinfectant stream from the disinfectant reservoir 26. Further, the control valve 30 is in fluid communication with the first segment 22 of the main conduit 20 (which is in communication with the water source).

For clarity, the control valves 30 and 31 may be referred to as a control valve assembly—essentially an umbrella term referring to the network of control valves operable to regulate the flow of water and disinfectant streams. The control valve assembly is operable to receive one of the disinfectant stream or water stream so that the received stream flows through the main conduit 20. The control valves 30 and 31 determine which stream is allowed to flow into the main conduit 20 via an electrical connection with the controller 36 (which also may be situated in a control housing (not shown). It is understood that the controller 36 may be hardware, i.e. predetermined electronics configured on a chip or may include a microprocessor in data communication with a non-volatile memory storing programming instructions. More particularly, the controller 36 is operable to actuate the control valves 30 and 31 to selectively allow the disinfectant stream or the water stream to flow downstream through the main conduit 20. In an embodiment, the control valves 30 and 31 may have a singular construction in communication with the water source 12, disinfectant reservoir 26, main conduit 20, and controller 36. Stated another way, a network of control valves electrically connected to the controller 36 and in fluid communication with the water source 12 and disinfectant reservoir 6 may be referred to, collectively, as "a control valve assembly" or "the control valve" with the context clearly indicating a reference to control valves 30 or 31. In another aspect, the controller 36 may be electrically connected to and in data communication with a control panel or touch screen (referred to as user controls 50) operable to receive and display instructions from a user.

A more detailed discussion of the specific algorithm executed by the controller 36 will be described later. It is understood that the controller 36 and other electric, electronic, and electromechanical components disclosed herein may be electrically connected to a power source 14 such as AC current, a battery, an inverter or the like.

In another aspect, a plurality of master nozzles 40 may be mounted at respected end points of the main conduit 20 as shown in the figures. Each master nozzle 40 may include a valve control assembly—essentially another or auxiliary controller 42 specifically operable or programmed to manage opening and closing of sprinkler and disinfectant nozzles at appropriate times. Each auxiliary controller 42 may be in data communication with the controller 36 first described above via wires or wirelessly so that instructions regarding which stream (water stream or disinfectant stream) are currently being directed downstream in the main conduit to be dispensed. It is understood that an auxiliary controller 42 operable a valve or valve actuator so as to actuator either an associated plurality of fire suppression dispersion nozzles 44 or plurality of mist nozzles 48.

Each master nozzle 40 includes a plurality of mist nozzles 48 in fluid communication with the main conduit 20 and operable for delivery of the disinfectant stream as a fine mist when actuated. Similarly, each master nozzle 40 includes a plurality of fire suppression dispersion nozzles 44 in fluid communication with said main conduit 20 and operable for delivery of said water stream, when actuated. To be clear, each master nozzle 40 includes both mist and fire suppression nozzles. The two nozzle types may include openings having different diameters and spray characteristics and may be positioned concentrically to enable independent and uninterrupted operation. A preferred embodiment of how the mist nozzles and fire suppression nozzles may be arranged is illustrated in FIG. 2a.

Fire suppression sprinkler systems have several common components and work generally as follows. In general, fire sprinklers work because high heat triggers the sprinkler system. Each sprinkler nozzle works individually. In other words, if one sprinkler nozzle is activated, the whole network of nozzles does not activate. When a blaze ignites, the air directly above it heats rapidly. This hot air rises and spreads along the ceiling. When the air is hot enough and reaches a sprinkler head, it triggers the respective head. Obviously, multiple sprinkler heads may trigger in rapid succession. Most sprinkler heads feature a glass bulb filled with a glycerin-based liquid. This liquid expands when it comes in contact with air heated to between 135 and 165 degrees. When the liquid expands, it shatters its glass confines and the sprinkler head activates. In the present application, the heat sensor (e.g. glass bulb) is represented by reference numeral 46. The heat sensor may also be referred to as a heat element or heat element valve.

Each sprinkler head includes a plurality of fire suppression dispersion nozzles 44 in fluid communication with the main conduit 20 that connects to the water source 12 as described above. It is important to note that when a respective fire suppression dispersion nozzle 44 is automatically actuated, its valves are opened automatically so as to deliver water onto the fire. FIG. 2c depicts a large mass of water being dropped onto a fire. Each dispersion nozzle 44 is in electrical communication with the auxiliary controller 42 associated therewith. Further, a respective auxiliary controller 42 is in electrical communication (with wires or wirelessly) with the controller 36 and control valve 30 described above such that a water stream is received into and allowed to flow downstream through the main conduit 20 to the plurality of fire suppression dispersion nozzles 44. It is understood that a pump 34 may be situated in the controller housing 38 and in fluid communication with the main conduit 20 and electrically connected to the controller 36 so as to pressurize the water stream. It is important that the water stream be pressurized so that it will be cast onto a fire automatically and with adequate force when a respective dispersion nozzle 44 is triggered. Further, the pressure combined with the configuration of the plurality of fire suppression dispersion nozzles 44 allows the water to spray outwardly in an arc to more thoroughly douse the fire and prevent it from reigniting.

Figure 1A:
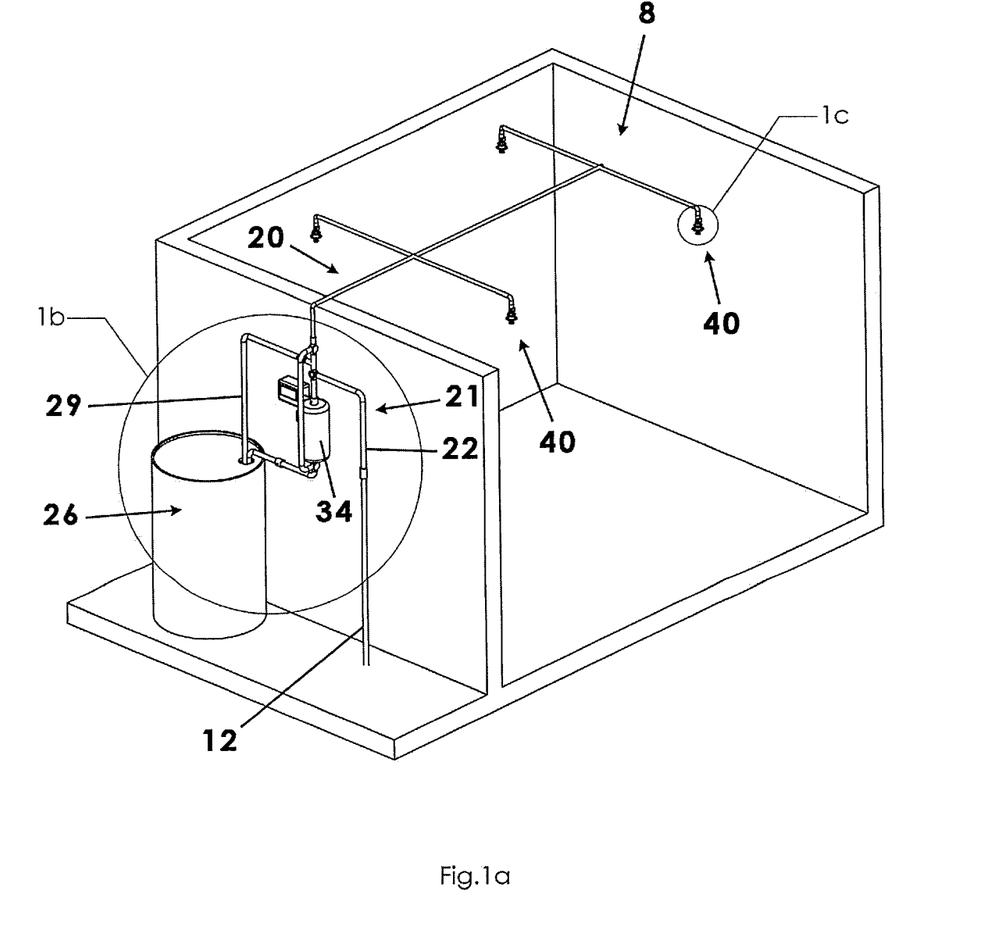
FIG. 1a is a perspective view of a disinfectant system according to an embodiment of the present invention, illustrated installed in a structure having a sprinkler system.
Figure 1B:
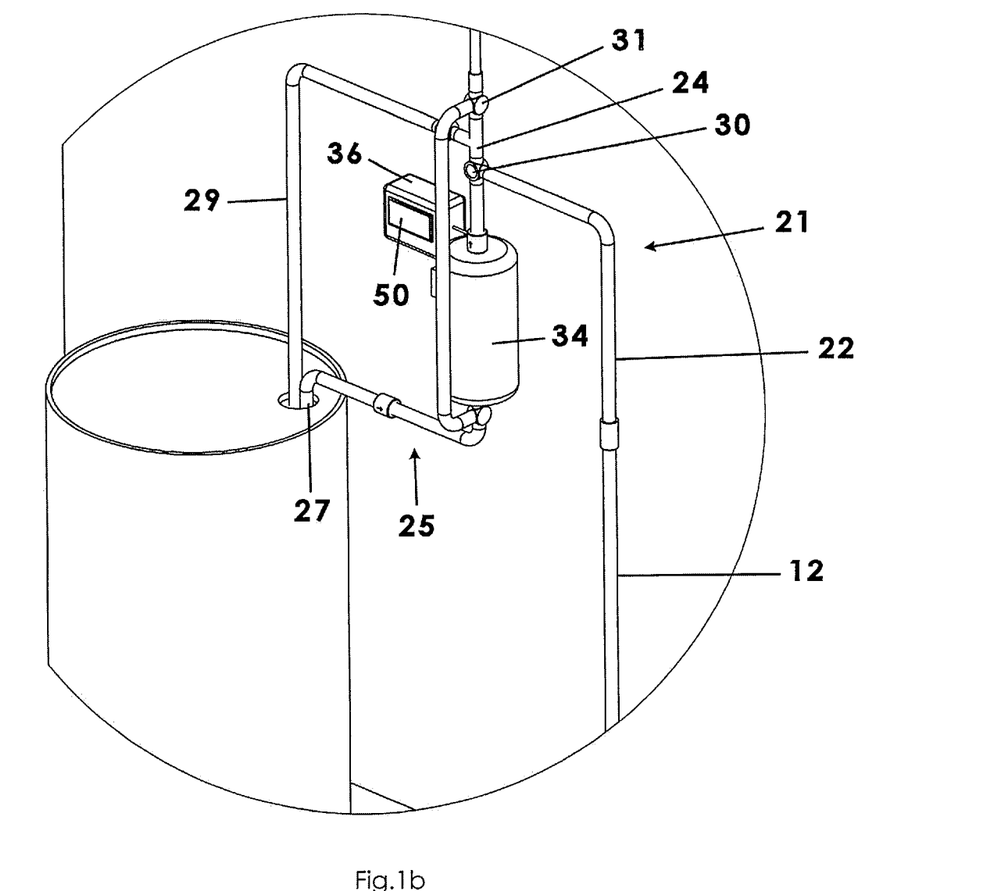
Figure 1C:
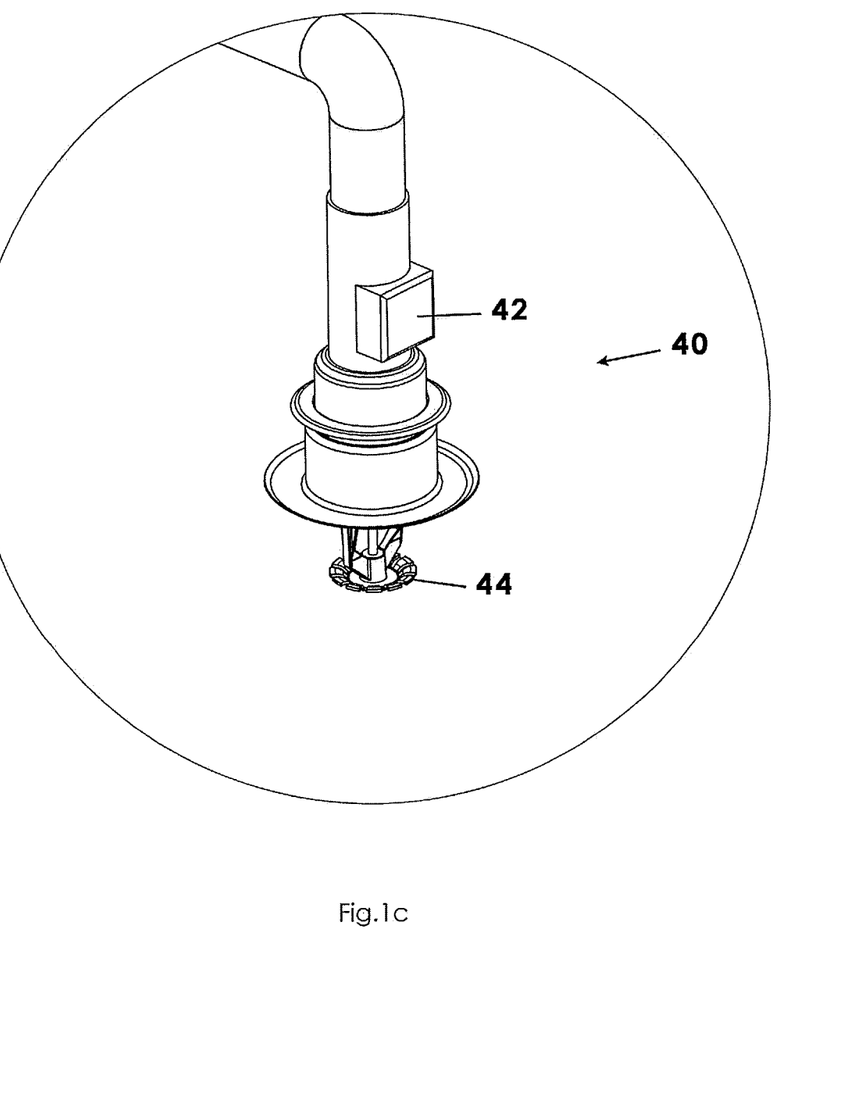
Figure 2A:
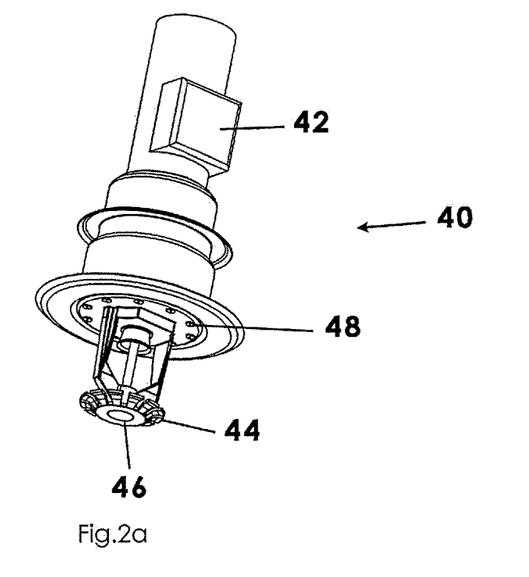
Figure 2B:
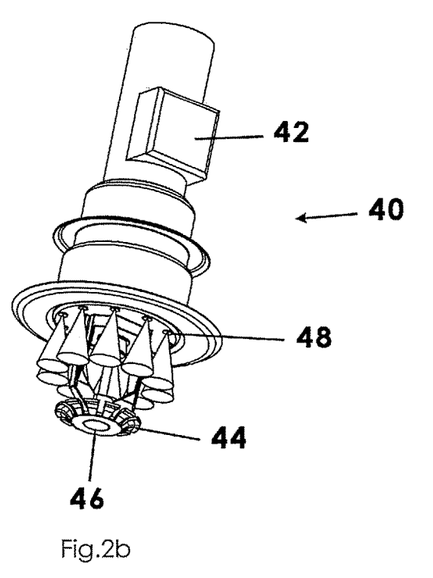
FIG. 2b is another bottom perspective view of a master nozzle as in FIG. 2a, illustrating operation of the mist nozzles.
Figure 2C:
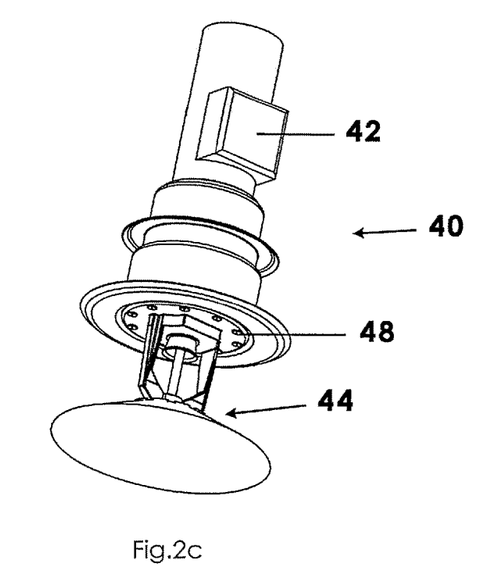
FIG. 2c is another bottom perspective view of a master nozzle as in FIG. 2a, illustrating operation of the sprinkler nozzles.
Figure 3:
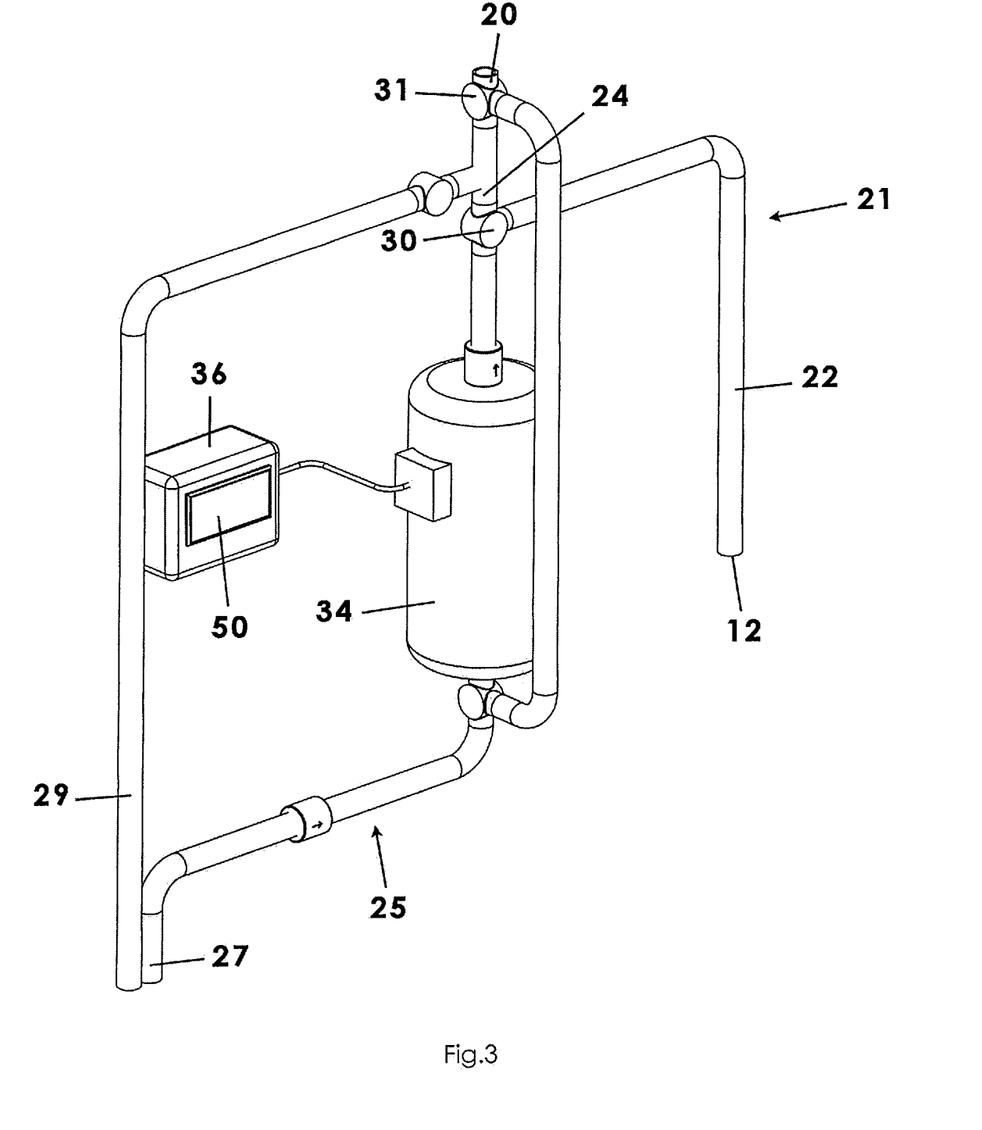
FIG. 3 is an isolated view on an enlarged scale taken from FIG. 1b.

Now, turning specifically to the mist nozzles 48, each master nozzle 40 may include a set or grouping of the plurality of mist nozzles 48 and which may be arranged in a circular pattern defining a diameter slightly larger than a diameter defined by the plurality of fire suppression dispersion nozzles 44 so as not conflict therewith (FIG. 2a). The auxiliary controller 42 associated with a respective master nozzle 40 is in data communication with an associated plurality of mist nozzles 48. Again, the auxiliary controller 42 is in data communication with controller 36 and control valve 30 described above such that a respective plurality of mist nozzles 48 may be actuated at said predetermined time and for operation for a predetermined time (i.e. a disinfectant cycle). FIG. 2b depicts the mist nozzles spraying disinfectant—using cone shaped characters to represent fine droplets for clarity. For instance, a preferred and predetermined time for a disinfectant cycle may be 2:00 a.m.—when no teachers or students are a classroom to be disinfected. Similar to the description relative to the plurality of fire suppression dispersion nozzles 44, a respective plurality of mist nozzles 48 is configured to allow a disinfectant stream to flow therethrough when actuated. As will be described later in more detail, the controller 36 may be programmed or electrically configured to stop a disinfectant cycle if a fire event is detected.

Before a disinfectant cycle may be executed, the water stream standing by in the main conduit 20 (i.e. in the "default mode"), must be evacuated and replaced by the disinfectant stream.

More particularly, an operational sequence may include preparing and spraying disinfectant. The cleaning cycle begins by the controller 36 actuating the pump 34 to draw water backwards from the main conduit 20 and plurality of fire suppression nozzles 44 and pump it back into the main water source 12. At the same time, the controller 36 is programmed or otherwise operable to actuate an opening of respective mist nozzles 48 to allow air into the system so that the water can be evacuated from the lines. When the water has been evacuated, the controller is configured to actuate the control valve 31 to allow the disinfectant stream to flow into the main conduit 20 as described above and to energize the pump 34 to pressurize the lines with the disinfectant fluid. Then the controller 36 may now signal all the sprinkler nozzles (or selected nozzles) to open their misting nozzles which spray the disinfectant into the room. After a predetermined length of time the controller 36 actuates the plurality of mist nozzles 48 to close, i.e. to stop misting the disinfectant stream.

Next, the controller 36 may actuate the pump 34 to reverse the disinfectant stream, returning it to the disinfectant reservoir 26 and purging the main conduit 20 in a manner substantially similar to the process described above. The controller 35 may be configured to open at appropriate times so that disinfectant travels through a disinfectant return conduit 29 and deposited in the reservoir 26. Once all the disinfectant fluid has been purged, the pump 34 is disabled along with the water cutoff valve which allows the pipes to once again be filled with water.

Figure 5:
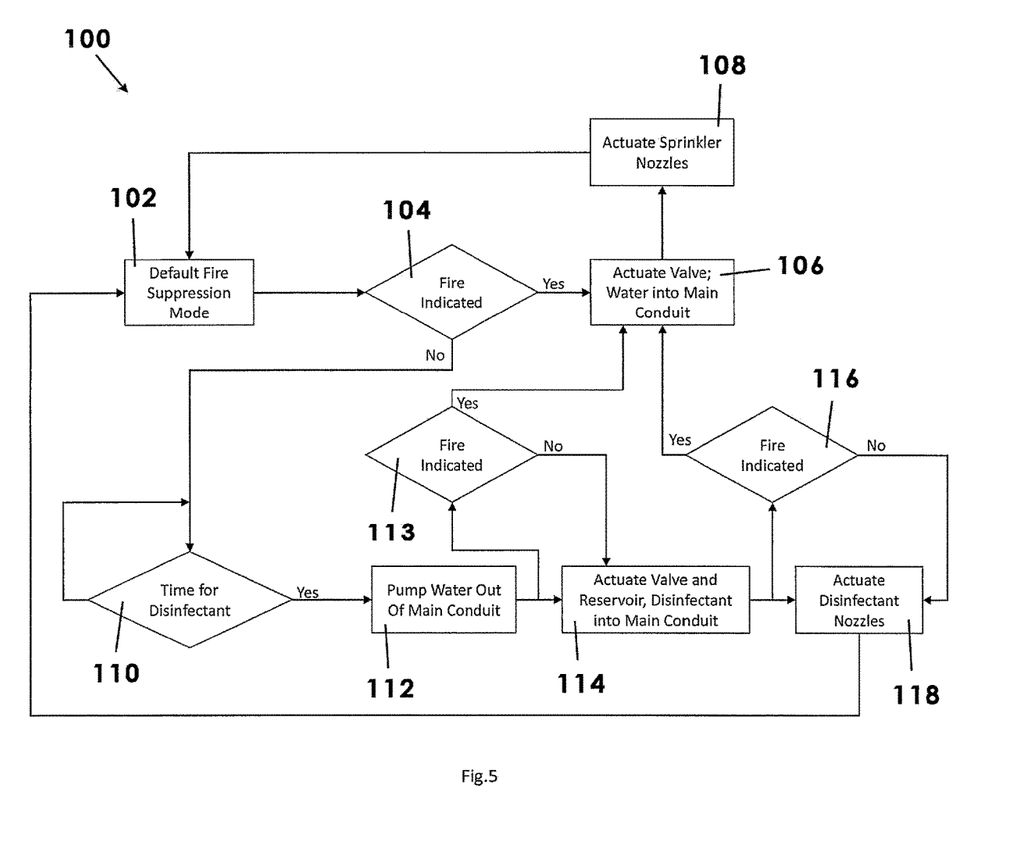
FIG. 5 is a flowchart illustrating a process executed according to the present invention.

The flowchart of FIG. 5 illustrates a process 100 and logic executed by the controller 36 described above. By default, the controller 36 begins in a default fire suppression mode as shown at block 102. The controller 36 stays in the default mode until a disinfectant mode is initiated and so long as no fire event is detected. In that regard, the controller 36 is configured to determine at step 104 if a fire event is detected. Specifically, if a respective fire suppression nozzle 44 is triggered as described above, the auxiliary controller 42 receives an alert signal and, correspondingly, the controller 36 receives the alert signal and the process proceeds to step 106; otherwise, the process 100 proceeds to step 110.

At step 106, the controller 36 is configured to actuate the control valve 30 to open and direct a water stream into the main conduit 20 as described above. The pump 34 may also be energized so as to pressurize the water stream flowing downstream toward the plurality of fire suppression dispersion nozzles 44. Process 100 proceeds to step 108 where one or more of the fire suppression dispersion nozzles 44 is actuated to allow the water stream to be dispersed on the fire. The process 100 may proceed to step 104 such that respective fire suppression dispersion nozzles 44 will continue to be activated and water made available so long as a fire event is indicated.

At step 110, the process 100 determines if it is time to initiate a disinfectant cycle (i.e. to enter a disinfectant mode). As described previously, the controller 36 may be programmed to determine a particular time each night (or at some other frequency) to carry out a disinfectant cycle. If the controller 36 determines it is time for a disinfectant cycle, the process 100 proceeds to step 112; otherwise, the process 100 proceeds to step 102 and returns to the default fire suppression mode. At step 112, the processor is configured to actuate the pump 34 to pump the water stream out of the main conduit 20 as described above. As fire suppression always takes priority, the process 100 proceeds to step 113 where the controller 36, in cooperation and in data communication with the auxiliary controller 42 and the plurality of fire suppression dispersion nozzles 44, determines if there is a fire event and, if so, the process 100 proceeds immediately and automatically to step 106 and the main conduit 20 is immediately filled with water and respective dispersion nozzles 44 are activated as described previously. But, if no intervening fire event is detected, process 100 proceeds to step 114.

At step 114, the controller 36 is programmed to actuate the control valve 31 to receive the disinfectant stream into the main conduit 20 to be directed downstream to the plurality of mist nozzles 48. Then, proceeding to step 116, a fire event is once again tested and, if found, control is immediately passed to step 106 to suppress the fire as described above; otherwise, the process 100 proceeds to step 118 where the controller 36, in cooperation with the auxiliary controller 42, is operable to actuate respective mist nozzles 48 to mist the disinfectant stream onto surfaces below (e.g. a classroom).

It is important to note here that the disinfectant fluid is non-flammable. If a fire event is detected, procedures for filling and pressurizing the main conduit 20 with water will occur automatically and immediately and may result in any of the disinfectant stream remaining in the main conduit 20 when the fire event is detected may get flushed through respective fire suppression dispersion nozzles. In other words, a non-flammable disinfectant stream will not aid the fire event. All components operate in a fail safe mode in that any malfunction will result in de-activation of the sanitization system and the fire suppression will function without any intervention.

It will be understood that while the flowchart shown in FIG. 5 illustrates stepwise determinations of whether a fire event is detected prior to or during a disinfectant cycle, the system may include electronics that are configured to simply interrupt or override a disinfectant cycle regardless of which step is being executed. Whenever a fire event is detected, the controller 36 will switch to an "emergency mode" and automatically pursue the procedures for fire suppression described above.

Accordingly, the disinfectant system 10 enables schools or the like to retrofit an existing fire suppression system (also known as a sprinkler system) to also perform a disinfectant cycle.

It is understood that while certain forms of this invention have been illustrated and described, it is not limited thereto except insofar as such limitations are included in the following claims and allowable functional equivalents thereof

The invention claimed is:

1. A disinfecting system for sanitizing a structure of a type having a fire suppression sprinkler system in fluid communication with a water source, said disinfecting system comprising:

- a main conduit positioned in the structure;
- a water assembly having a first segment in fluid communication with the water source and operable to carry a water stream downstream from the water source, said water assembly having a second segment downstream from said first segment and that is in fluid communication with said main conduit;
- a disinfectant reservoir operable to contain a volume of liquid disinfectant;
- a disinfectant assembly that includes a disinfectant conduit having a first end in fluid communication with said disinfectant reservoir and operable to carry a disinfectant stream downstream from said disinfectant reservoir, said disinfectant conduit having a second end downstream from said first end and that is in fluid communication with said main conduit;
- a control valve assembly positioned inline in said water assembly and in fluid communication with said second end of said disinfectant conduit and in fluid communication with said first segment of said main conduit, said control valve assembly being configured to allow one of said disinfectant stream or said water stream to flow downstream in said main conduit;
- a controller in data communication with said control valve assembly that is configured to determine whether to actuate said control valve assembly to selectively allow said disinfectant stream or said water stream to flow downstream in said main conduit; and
- a master nozzle having a plurality of outlet holes situated along and in fluid communication with said main conduit, said master nozzle being positioned downstream of said control valve and operably configured to spray a liquid into an interior area of the structure;
- wherein said master nozzle defines:
  - a plurality of mist nozzles in fluid communication with said main conduit operable for delivery of said disinfectant stream as a fine mist;
  - a plurality of fire suppression dispersion nozzles in fluid communication with said main conduit and operable for delivery of said water stream;
  - an auxiliary controller in data communication with said controller and configured to connect in fluid communication one of said plurality of mist nozzles and said plurality of fire suppression dispersion nozzles to said main conduit, respectively, when said connection is determined by said controller;
  - wherein said master nozzle has a unitary construction that defines a respective fire suppression dispersion nozzle and a set of said plurality of mist nozzles;
  - wherein said controller is configured to allow said water stream to flow immediately downstream in said main conduit when a respective heat element valve indicates detection of a fire event;
  - wherein said controller is configured to immediately prevent said disinfectant stream from moving downstream in said main conduit when said respective heat element valve indicates detection of a fire event;
  - wherein said controller is configured to actuate a pump to reverse a direction of fluid flow of said liquid disinfectant, said liquid disinfectant being urged upstream from said main conduit and into said disinfectant reservoir.

2. The disinfectant system as in claim 1, wherein each fire suppression nozzle includes a heat element valve operable to detect a rising temperature, said heat element valve being in data communication with said controller and configured to place said controller in an emergency mode immediately when said heat element valve detects a fire event.

3. The disinfectant system as in claim 1, wherein said disinfectant stream is a non-flammable fluid.

4. The disinfectant system as in claim 1, wherein said controller includes a timer configured to initiate a disinfectant mode at a predetermined interval of time, said controller configured to actuate said control valve assembly to allow said disinfectant stream to flow downstream in said main conduit when said controller is in said disinfectant mode.

5. The disinfectant system as in claim 4 wherein said timer is configured to determine an end time for said disinfectant mode and to actuate a return of said disinfectant stream to said disinfectant reservoir.

6. The disinfectant system as in claim 5, wherein said controller is configured to revert to a fire suppression mode at said end time associated with said disinfectant mode, said fire suppression mode being a default mode.

7. The disinfectant system as in claim 4, wherein said controller is configured to automatically and immediately evacuate said main conduit when said controller is put in said disinfectant mode.

8. The disinfectant system as in claim 7, wherein said controller is configured to actuate said plurality of mist nozzles to an open configuration simultaneously with said evacuation of said main conduit.

9. The disinfectant system as in claim 1, wherein said controller is configured to actuate said pump to reverse a direction of fluid flow of said water stream, said water stream being urged upstream from said main conduit to said water source.

\* \* \* \* \*